United States Patent [19]

Nagato et al.

[11] Patent Number: 4,567,292
[45] Date of Patent: Jan. 28, 1986

[54] PROCESS FOR PRODUCTION OF ALLYL CARBOXYLATE

[75] Inventors: Nobuyuki Nagato, Saitama; Kenichiro Maki, Kanagawa; Tomoe Uematsu, Kanagawa; Ryoji Ishioka, Kanagawa, all of Japan

[73] Assignee: Showa Denko Kabushiki Kaisha, Tokyo, Japan

[21] Appl. No.: 695,024

[22] Filed: Jan. 25, 1985

[51] Int. Cl.$^4$ ............................................. C07C 67/05
[52] U.S. Cl. ..................................... 560/245; 502/170
[58] Field of Search ........................................ 560/245

[56] References Cited

U.S. PATENT DOCUMENTS

| | | | |
|---|---|---|---|
| 3,417,133 | 12/1968 | Harris | 560/243 |
| 3,609,180 | 9/1971 | Shigematsu | 560/243 |
| 4,365,082 | 12/1982 | Laloz | 560/243 |

FOREIGN PATENT DOCUMENTS

| | | | |
|---|---|---|---|
| 43-7207 | 3/1968 | Japan | 560/243 |
| 44-24089 | 10/1969 | Japan | 560/243 |
| 45-7724 | 3/1970 | Japan | 560/243 |

*Primary Examiner*—Michael L. Shippen
*Attorney, Agent, or Firm*—Sughrue, Mion, Zinn, Macpeak & Seas

[57] ABSTRACT

A process for producing an allyl carboxylate comprising the step of reacting propylene, oxygen or oxygen-containing gas, and a lower saturated carboxylic acid in the presence of a catalyst at a temperature of 100° C. to 300° C. and a pressure of 0 to 30 atm (gauge) in a vapor phase. The catalyst is prepared by supporting, on a carrier, at least one alkali metal acetate and at least one bivalent palladium salt in the presence of: (A) at least one organic base selected from the group consisting of (i) aliphatic amines having the formula:

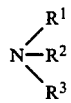

wherein $R^1$, $R^2$, and $R^3$ may be the same or different and represent hydrogen, or an alkyl group having 1 to 10 carbon atoms or benzyl group optionally substituted with —CN, —OR, —COOR, or a —N(R)$_2$ group wherein R is H or an alkyl group having 1 to 3 carbon atoms, or any two groups of $R^1$, $R^2$, and $R^3$ may together form a ring provided that $R^1$, $R^2$, and $R^3$ are not simultaneously hydrogen; (ii) aromatic amines having the formula:

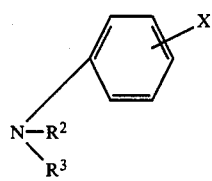

wherein X represent —R, —CN, —OR, —COOR, —NO$_2$, or —N(R)$_2$ wherein R is the same as defined above, $R^2$ and $R^3$ are the same as defined above; and (iii) nitrogen-containing cyclic compounds having the formula:

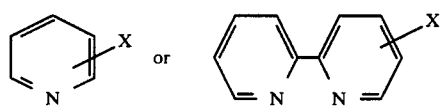

wherein X is the same as defined above; and/or (B) at least one carboxylic acid having the formula:

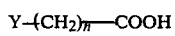

Y—(CH$_2$)$_n$—COOH wherein Y represents —OR, —CN, —COOR, —CH(R)NH$_2$, —COR, —N(CH$_2$COOH)$_2$, —NHCH$_2$COOH, or —CH(R$^1$)X group wherein R, R$^1$, and X are the same as defined in (A) above, and n is an integer of 1 to 4.

This catalyst has a high activity and a long durability and can produce the desired allyl carboxylate at a high selectivity.

4 Claims, No Drawings

PROCESS FOR PRODUCTION OF ALLYL CARBOXYLATE

BACKGROUND OF THE INVENTION

1. Field of the Invention

The present invention relates to a process for producing an allyl ester of carboxylic acid (i.e., allyl carboxylates). More specifically, it relates to a process for producing an allyl carboxylate from a vapor phase reaction of propylene, oxygen (or oxygen-containing gas) and a lower saturated carboxylic acid.

2. Description of the Related Art

It is known in the art that allyl carboxylates are produced by the vapor phase oxidation of propylene in the presence of lower saturated carboxylic acids by using, as a catalyst, metallic palladium or palladium salts and other additives such as alkali or alkaline earth metal salts supported on a carrier. It is also known that metallic salts such as salts of gold, bismuth, iron, copper, vanadium, manganese, chromium, and molybdenium can be used as a cocatalyst in the above-mentioned vapor phase oxidation.

When the above-mentioned cocatalysts are not used, i.e., when palladium-alkali metal salt catalysts are used, the desired allyl carboxylates still can be obtained to some extent. However, since a large amount of by-products, especially gaseous carbon dioxide, are produced, selectivity to the desired allyl carboxylates is limited. Although the amount of the carbon dioxide byproduct produced can be decreased by lowering the reaction temperature, the formation rate of the desired allyl carboxylates is thereby unpreferably decreased which is not desirable from the viewpoint of industrial production. On the other hand, when a cocatalyst such as a copper salt is used in the above-mentioned vapor phase oxidation reaction, the amount of the carbon dioxide byproducts produced is decreased. However, the formation rate of the desired allyl carboxylates is thereby unpreferably decreased, and it is believed in the art, the catalyst activity is impaired for a relatively short period of time.

Various attempts have been made to improve these disadvantages of the above-mentioned vapor phase oxidation reaction. For example, the addition of a copper salt or vanadium salt of compounds having the formula:

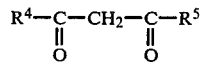

wherein $R^4$ and $R^5$ are independently an aliphatic, aromatic, or alkoxyl group, to the reaction system has been proposed. However, although this proposed process has been found effective in the case of, for example, the salts of acetylacetone, it is not suitable as an industrial process because the use of the special agent is required.

SUMMARY OF THE INVENTION

An object of the present invention is to eliminate the above-mentioned disadvantages of the prior art and to provide a process for producing an allyl carboxylate from propylene and a lower saturated carboxylic acid at a high selectivity by using a catalyst containing palladium and an alkali metal salt and, optionally, a copper salt, having a high activity and long durability.

Other objects and advantages of the present invention will be apparent from the following description.

In accordance with the present invention, there is provided a process for producing an allyl carboxylate comprising the step of reacting propylene, oxygen, or oxygen-containing gas, and a lower saturated carboxylic acid in the presence of a catalyst at a temperature of 100° C. to 300° C. and a pressure of 0 to 30 atm (gauge) in a vapor phase. This catalyst is prepared by supporting, on a carrier, at least one alkali metal acetate and at least one bivalent palladium salt in the presence of:

(A) at least one organic base selected from the group consisting of (i) aliphatic amines having the formula:

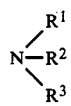

wherein $R^1$, $R^2$, and $R^3$ may be the same or different and represent hydrogen, or an alkyl group having 1 to 10 carbon atoms, or a benzyl group optionally substituted with —CN, —OR, —COOR, or a —N(R)$_2$ group wherein R is H or an alkyl group having 1 to 3 carbon atoms, or any two groups of $R^1$, $R^2$, and $R^3$ may together form a ring provided that $R^1$, $R^2$, and $R^3$ are not simultaneously hydrogen; (ii) aromatic amines having the formula:

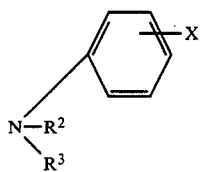

wherein X represents —R, —CN, —OR, —COOR, —NO$_2$, or —N(R)$_2$, wherein R is the same as defined above, $R^2$ and $R^3$ are the same as defined above; and (iii) nitrogen-containing cyclic compounds having the formula:

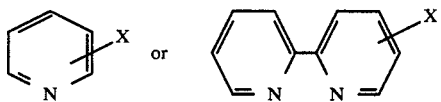

wherein X is the same as defined above; and/or (B) at least one carboxylic acid having the formula:

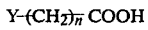

wherein Y represents —OR, —CN, —COOR, —CH(R)NH$_2$, —COR, —N(CH$_2$COOH)$_2$, —NHCH$_2$COOH, or a —CH($R^1$)X group wherein R, $R^1$, and X are the same as defined in (A) above, and n is an integer of 1 to 4.

DESCRIPTION OF THE PREFERRED EMBODIMENTS

According to the present invention, the desired allyl carboxylate can be prepared at a high selectivity and production rate by using a catalyst prepared by supporting, on a carrier, an alkali metal acetate and a bivalent palladium salt and, optionally, a copper salt, together with the specified organic base and/or carboxylic acid.

The alkali metal acetates usable in the preparation of the catalyst used in the present invention are, for example, lithium, sodium, and potassium acetates. Of these alkali metal acetates, the use of potassium is preferable. These alkali metal acetates can be used alone or in any mixture thereof. Although there is no critical limitation to the amount of the alkali metal acetates, the alkali metal acetates are used in an amount of 20~70 g per one liter of the carrier.

The bivalent palladium salts usable in the preparation of the catalyst used in the present invention are the bivalent palladium salts such as palladium chloride, palladium nitrate, and palladium acetate. Of these bivalent palladium salts, palladium acetate is preferably used. These bivalent palladium salts can be used alone or in any mixture thereof.

The copper salts optionally usable, together with the alkali metal acetates and the bivalent palladium salts, in the preparation of the catalyst used in the present invention are, for example, copper hydroxide, copper acetate, and the copper salts of carboxylic acids having the formula:

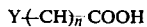

wherein Y and n are the same as defined above. Of these copper salts, the use of copper acetate is preferable. These copper salts can be used alone or in any mixture thereof. Although there is no critical limitation to the amount of the copper salts, the copper salts are used in an amount of 0.5 to 10.0 g, preferably 1.0~5.0 g as the copper metal based on one liter of the carrier.

The organic bases in the preparation of the catalyst used in the present invention are primary, secondary, and tertiary aliphatic amines, aromatic amines, and nitrogen-containing cyclic compounds. Polyamines such as ethylene diamine and substituted amines such as ethanol amine also may be used in the present invention. However, the use of substituted amines having halogen- or sulfur-containing substituents is not appropriate, and $NH_3$ is not substantially effective.

Examples of suitable organic bases are aliphatic amines such as methylamine, ethylamine, n-propylamine, iso-propylamine, n-butylamine, dimethylamine, diethylamine, di-n-propylamine, di-iso-propylamine, di-n-butylamine, trimethylamine, triethylamine, tri-n-propylamine, tri-n-butylamine, cyclohexylamine, benzylamine, piperidine, 3-methylpiperidine, 4-methylpiperidine, piperadine, 2,5-dimethylpiperadine, morpholine, ethanolamine, diethanolamine, triethanolamine, β-cyanoethylamine, bis-(β-cyanoethyl)amine, β-alanine methylester, ethylenediamine, and diethylenetriamine; aromatic amines such as aniline, N-methylaniline, N,N-dimethylaniline, p-toluidine, m-toluidine, o-toluidine, p-nitroaniline, m-nitroaniline, o-nitroaniline, p-methoxyaniline, m-methoxyaniline, o-methoxyaniline, p-phenylene diamine, m-phenylenediamine, and o-phenylene diamine; and pyridines such as pyridine, α-picoline, β-picoline, γ-picoline, methylethyl pyridines, β-cyanopyridine, methyl nicotinate, and 2,2'-bipyridyl. These organic bases can be used alone or in any mixture thereof.

These organic bases are preferably used in the catalyst in an atomic ratio of N/Pd of 0.5 to 20, especially 1 to 10. When the copper salts are also used in the catalyst, the preferable atomic ratio of N/(Pd+Cu) can be within the above-mentioned range.

The carboxylic acids usable alone, or together with the above-mentioned organic bases, in the preparation of the catalyst usable in the present invention are those having the formula.

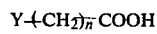

Preferable carboxylic acids having the above-mentioned general formula wherein n=1 are those having the substituent Y of —COOH, —CN, and —OH groups. Typical examples of the preferable carboxylic acids are glycolic acid, methoxyacetic acid, β-hydroxypropionic acid, cyanoacetic acid, malonic acid, monomethyl malonate, succinic acid, adipic acid, citric acid, β-alanine, acetoacetic acid, iminodiacetic acid, and nitrilotriacetic acid. These carboxylic acids can be used alone or in any mixtures thereof.

These carboxylic acids are preferably used in the catalyst in an amount of a carboxylic acid group/Pd atom of 0.5 to 10, especially 1 to 5. When the copper salts are used, together with the bivalent palladium salts, in the catalysts, the copper salts are preferably used in an amount of a carboxyl group/Pd+Cu of 0.5 to 10, especially 1 to 5. Furthermore, when the carboxylic acids are used together with the above-mentioned organic bases in the catalyst, both the carboxylic acids and the organic bases are preferably used in the above-mentioned ranges of the amounts, respectively.

The catalysts used in the present invention can be prepared in any conventional manner. For example, the above-mentioned catalyst components are dissolved in a solvent to form a uniform solution, and carriers are then impregnated with the uniform solution. When the solvent is present in an excess amount, the excess solvent is evaporated upon heating under an ambient pressure or reduced pressure. Thus, the catalyst components are supported on the carriers. After drying, the catalysts are calcined and, if desired, the calcined catalysts are then reduced. The evaporation of the solvent and the drying may be carried out at a temperature sufficient to evaporate the solvent. The calcination can be carried out at a temperature of, for example, 120° C. to 400° C., preferably 150° C. to 300° C., under air, preferably nitrogen. The reduction can be carried out in an atmosphere of hydrogen or an unsaturated hydrocarbon such as ethylene or propylene, after or simultaneously with the calcination. Alternatively, the reduction may be carried out, prior to the reaction, in an atmosphere of starting gases excluding oxygen (or oxygen-containing gas). However, most of the palladium compound is reduced during the calcination step and, therefore, it may not be necessary to carry out the above-mentioned reduction operation.

The carriers used in the preparation of the catalysts usable in the present invention can be any conventional carriers such as activated carbon, titanium dioxide, alumina, silica, and zirconium oxide. Silica is preferably used in the present invention.

The production of the desired allyl carboxylates according to the present invention can be carried out at a temperature of 100° C. to 300° C., preferably 120° C. to 210° C. under a pressure of 0 to 30 atm (gauge), preferably 2 to 10 atm (gauge), by packing the above-mentioned catalysts in an appropriate reactor, followed by feeding the starting gas mixture. The composition of the starting gas mixture to be fed to the reactor can be varied within a wide range. For example, although the ratio of the propylene, oxygen or oxygen-containing gas (e.g., air or oxygen/carbon dioxide mixture), and lower saturated carboxylic acid is not specifically limited, such ratio is preferably used that propylene; oxygen and carboxylic acid are 10–40:3–10:3–20 molar).

The lower saturated carboxylic acids used in the present invention depend upon the allyl carboxylates desired. Typical examples of the lower saturated carboxylic acids are saturated aliphatic carboxylic acids having 2 to 5 carbon atoms such as acetic acid, propionic acid, butyric acid, isobutyric acid valeric acid, isovaleric acid and pivalic acid. The oxygen (or oxygen-containing gas) is preferably used in an amount such that the concentration in the vapor reaction system is out of the explosive range of oxygen. Various inert gas such as $N_2$, $CO_2$ $H_2O$, and saturated hydrocarbons (e.g., propane) may be present in the reaction system. Although there is no special limitation to the amount of the catalyst to be used in the reaction, $1000 \sim 10000$ $hr^{-1}$ (l/cat l/hr), preferably $1500 \sim 5000$ $hr^{-1}$ are used.

According to the present invention, the desired allyl carboxylate having 2 to 5 carbon atoms can be prepared at an extremely high selectivity and a high space time yield by reacting the propylene, oxygen (or oxygen-containing gas), and lower saturated carboxylic acid in the presence of the above-mentioned catalyst at an elevated temperature and pressure. Furthermore, the high activity and high selectivity of the above-mentioned reaction can be continued for a long reaction period.

EXAMPLES

The present invention will now be further illustrated by, but is by no means limited to, the following examples, all percentages are expressed on a molar basis unless otherwise specified.

EXAMPLE 1

A 2.3 g amount of potassium acetate was dissolved in 20 ml of acetic acid, while heating the acetic acid to a temperature of 90° C. Then, 0.65 g palladium acetate, 0.66 g glycolic acid, and 0.69 g of pyridine were added to the solution and dissolved therein. To the uniform solution thus obtained, 50 ml of silica having a particle size of 5 mm was added and agitated so as to be uniformly impregnated with the solution. The impregnated product was heated, while stirring, to a temperature of 120° C. to 130° C. to evaporate the solvent, followed by drying for a further 30 minutes. Thereafter, the impregnated product was calcined at a temperature of 160° C. to 170° C. for 2 hours under a nitrogen stream to prepare a catalyst.

A 20 ml amount of the catalyst prepared above was packed in a stainless steel reaction tube having an inner diameter of 15 mm. Then, a starting gas mixture of 55.8 vol% of nitrogen, 20 vol% of propylene, 4.9 vol% of oxygen, 5.3 vol% of acetic acid, and 14.0 vol% of water was continuously fed to the reaction tube at a rate of 97.6 Nl/hr (i.e., S.V.=4880/hr). Thus, the vapor phase oxidation reaction was carried out at a heating bath temperature of 145° C. under a pressure of 5.0 atm (gauge).

The formation rate of the desired allyl acetate was 423 g/hr based on 1 liter of the catalyst after 16 hours from the start of the reaction. The selectivity to the allyl acetate was 94.1%.

EXAMPLE 2

A catalyst was prepared in the same manner as in Example 1, except that the pyridine was not used. The oxidation reaction was carried out in the same manner as in Example 1 by using the catalyst thus prepared.

The formation rate of the desired allyl acetate was 335 g/hr based on one liter of the catalyst after 16 hours from the start of the reaction. The selectivity to the allyl acetate was 94.6%.

EXAMPLE 3

A catalyst was prepared in the same manner as in Example 1, except that 0.40 g of ethylenediamine was used instead of the glycolic acid and pyridine. The oxidation reaction was carried out in the same manner as in Example 1 by using the catalyst thus prepared.

The formation rate of the desired allyl acetate was 345 g/hr based on one liter of the catalyst after 16 hours from the start of the reaction. The selectivity to the allyl acetate was 94.0%.

COMPARATIVE EXAMPLE 1

A catalyst was prepared in the same manner as in Example 1, except that the glycolic acid and pyridine were not used. The oxidation reaction was carried out in the same manner as in Example 1 by using the catalyst thus prepared.

The formation rate of the desired allyl acetate was 169 g/hr based on one liter of the catalyst after 16 hours from the start of the reaction. The selectivity to the allyl acetate was 94.5%. Furthermore, when the heating bath temperature was increased to 165° C., the formation rate of the desired allyl acetate was increased to 295 g/hr based on one liter of the catalyst after 16 hours from the start of the reaction, but the selectivity to the allyl acetate was 90.3%.

EXAMPLE 4

A 2.3 g amount of potassium acetate was dissolved in 20 ml of acetic acid. Then, after 0.65 g of palladium acetate, and 0.364 g of copper acetate were dissolved, 0.764 g of malonic acid and 0.70 g of ethylenediamine were added to the solution and dissolved therein. To the uniform solution thus obtained, 50 ml of silica having a particle size of 5 mm was added and agitated so as to be uniformly impregnated with the solution. The impregnated product was heated, while stirring, to a temperature of 120° C. to 130° C. evaporate the solvent, followed by drying for further 30 minutes. Thereafter, the impregnated product was calcined at a temperature of 160° C. to 170° C. for 2 hours under a nitrogen stream to prepare a catalyst.

A 15 ml amount of the catalyst prepared above was packed in a stainless steel reaction tube having an inner diameter of 21 mm. Then, the gas mixture having the same composition as used in Example 1 was continuously fed to the reaction tube at a feed rate of 36 Nl/hr (i.e., S.V.=2400/hr). Thus, the vapor phase oxidation reaction was carried out under a pressure of 5.0 atm (gauge). The temperature within the reaction tube was 195° C. for first 5 hours after the start of the reaction, 185° C. for a further 5 hour period, and 175° C. for the last 15 hours.

The formation rate of the desired allyl acetate was 302 g/hr based on 1 liter of the catalyst. The selectivity to the allyl acetate was 92%.

COMPARATIVE EXAMPLE 2

A catalyst was prepared in the same manner as in Example 4, except that 0.847 g (i.e., the same mole number as the palladium acetate) of tetraammine palladium acetate (NH$_3$)$_4$ Pd(OAc)$_2$ was used instead of 0.65 g of the palladium acetate and that the malonic acid and ethylenediamine were not used, but 0.79 g of a 25% aqueous ammonia was added.

The oxidation reaction of Example 4 was repeated by using 15 ml of the catalyst prepared above.

The formation rate of the desired allyl acetate was 177 g/hr based on one liter of the catalyst. The selectivity to the allyl acetate was 89%.

EXAMPLE 5

A catalyst was prepared in the same manner as in Example 3, except that 1.2 g of aniline was used instead of 0.40 g of the ethylenediamine and the catalyst calcination temperature was changed to 190° C. The oxidation reaction was carried out in the same manner as in Example 3 by using 20 ml of the catalyst thus prepared.

The formation rate of the desired allyl acetate was 322 g/hr based on one liter of the catalyst after 16 hours from the start of the reaction. The selectivity to the allyl acetate was 94.0%.

EXAMPLE 6

A catalyst was prepared in the same manner as in Example 1, except that 0.74 g of cyanoacetic acid and 0.64 g of diethylamine was used instead of glycolic acid and pyridine. The oxidation reaction was carried out in the same manner as in Example 1 by using the catalyst thus prepared.

The formation rate of the desired allyl acetate was 416 g/hr based on one liter of the catalyst after 16 hours from the start of the reaction. The selectivity to the allyl acetate was 94.4%.

EXAMPLE 7

A catalyst was prepared in the same manner as in Example 1, except that 0.51 g of succinic acid and 0.53 g of ethanolamine were used instead of the glycolic acid and pyridine, respectively. The oxidation reaction was carried out in the same manner as in Example 1 by using the catalyst thus prepared.

The formation rate of the desired allyl acetate was 402 g/hr based on one liter of the catalyst after 6 hours from the start of the reaction. The selectivity to the allyl acetate was 94.2%.

EXAMPLE 8

A catalyst were prepared in the same manner as in Example 1, except that 0.58 g of iminoacetic acid and 0.74 g of piperidine were used instead of the glycolic acid and pyridine.

A 20 ml amount of the catalyst prepared above was packed in a stainless steel reaction tube having an inner diameter of 15 mm. Then, a gas mixture of 48 vol% of nitrogen, 30 vol% of propylene, 7 vol% of acetic acid, 10 vol% of water, and 5 vol% of oxygen was continuously fed to the reaction tube at a rate of 97.6 Nl/hr. Thus, the vapor phase oxidation reaction was carried out at a heating bath temperature of 155° C. under a pressure of 5.0 atm (gauge).

The formation rate of the desired allyl acetate was 485 g/hr based on 1 liter of the catalyst and the selectivity to the allyl acetate was 94.2%.

EXAMPLE 9

A catalyst was prepared in the same manner as in Example 8, except that 0.61 g citric acid and 0.49 g of β-cyanoethylamine were used instead of the iminodiacetic acid and piperidine, respectively. The oxidation reaction was carried out in the same manner as in Example 8 by using the catalyst thus prepared.

The formation rate of the desired allyl acetate was 470 g/hr based on one liter of the catalyst after 30 hours from the start of the reaction. The selectivity to the allyl acetate was 94.5%.

EXAMPLE 10

A catalyst was prepared in the same manner as in Example 4, except that 0.77 g of β-aminopropionic acid and 0.68 g of 2,2′-bipyridyl were used instead of the malonic acid and ethylenediamine, respectively. The catalyst supported on the silica carrier, after drying, was calcined under a nitrogen atmosphere for 1.5 hours at a temperature of 160° C. to 170° C. and for 30 minutes at a temperature of 230° C.

The oxidation reaction of Example 4 was carried out by using 15 ml of the catalyst prepared above.

The formation rate of the desired allyl acetate was 310 g/hr based on one liter of the catalyst 20 hours after the reaction temperature was reached to 175° C. The selectivity to the allyl acetate was 91.7%.

EXAMPLE 11

A 23 g amount of potassium acetate was dissolved in 200 ml of acetic acid. Then, 5.6 g glycolic acid, 6.5 g of palladium acetate, 3.64 g of copper acetate, and 7.0 g of ethylene diamine were added to the solution and dissolved therein. To the uniform solution thus obtained, 500 ml of silica having a particle size of 2 to 3 mm was added and agitated so as to be uniformly impregnated with the solution. The impregnated product was dried at a temperature of 120° C. to 130° C. for 30 minutes. Thereafter, the impregnated product was calcined at a temperature of 160° C. to 170° C. for 2 hours under a nitrogen stream.

A 500 ml amount of the catalyst prepared above was packed in a stainless steel reaction tube having an inner diameter of 28 mm. Then, a gas mixture of 50.8 vol% of nitrogen, 25 vol% of propylene, 4.9 vol% of oxygen, 5.3 vol% of acetic acid, and 14.0 vol% of water was continuously fed to the reaction tube at a feed rate of 1.2 Nm$^3$/hr. Thus, the vapor phase oxidation reaction was carried out at a maximum temperature within the reaction tube of 176° C. under a pressure of 4.5 atm (gauge).

The formation rate of the desired allyl acetate was 410 g/hr based on 1 liter of the catalyst after 150 hours from the start of the reaction. The selectivity to the allyl acetate was 95.7%. These formation rate and selectivity were not substantially changed after 1500 hour continuous reaction.

We claim:

1. A process for producing an allyl carboxylate comprising the step of reacting propylene, oxygen or oxygen-containing gas, and a lower saturated carboxylic acid in the presence of a catalyst at a temperature of 100° C. to 300° C. and a pressure of 0 to 30 atm (gauge) in a vapor phase, said catalyst being prepared by supporting, on a carrier, at least one alkali metal acetate and at least one bivalent palladium salt in the presence of:
   (A) at least one organic base selected from the group consisting of
       (i) aliphatic amines having the formula:

wherein R¹, R², and R³ may be the same or different and represent hydrogen, or an alkyl group having 1 to 10 carbon atoms or benzyl group optionally substituted with —CN, —OR, —COOR, or a —N(R)₂ group wherein R is H or an alkyl group having 1 to 3 carbon atoms, or any two groups of R¹, R², and R³ may together form a ring provided that R¹, R², and R³ are not simultaneously hydrogen;

(ii) aromatic amines having the formula:

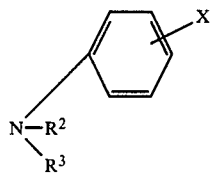

wherein X represent —R, —CN, —OR, —COOR, —NO₂, or —N(R)₂ wherein R is the same as defined above, R² and R³ are the same as defined above; and (iii) nitrogen-containing cyclic compounds having the formula:

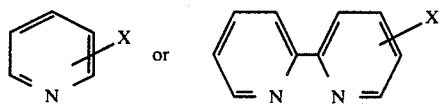

wherein X is the same as defined above; and/or (B) at least one carboxylic acid having the formula:

Y—(CH₂)ₙ̄ COOH wherein Y represents —OR, —CN, —COOR, —CH(R)NH₂, —COR, —N(CH₂COOH)₂, —NHCH₂COOH, or —CH(R¹)X group wherein R, R¹, and X are the same as defined in (A) above, and n is an integer of 1 to 4.

2. A process as claimed in claim 1, wherein at least one copper salt is used together with the bivalent palladium salt.

3. A process as claimed in claim 1, wherein the organic base is used in an atomatic ratio of N/Pd of 0.5 to 20 in the catalyst.

4. A process as claimed in claim 1, wherein the carboxylic acid is used in a ratio of a carboxylic acid group/Pd atom of 0.5 to 10 in the catalyst.

* * * * *